United States Patent [19]

Smits

[11] Patent Number: 4,938,742

[45] Date of Patent: Jul. 3, 1990

[54] PIEZOELECTRIC MICROPUMP WITH MICROVALVES

[76] Inventor: Johannes G. Smits, 22 Farrell St., Quincy, Mass. 02169

[21] Appl. No.: 152,379

[22] Filed: Feb. 4, 1988

[51] Int. Cl.⁵ ............................................. A61M 31/00
[52] U.S. Cl. ...................................... 604/67; 222/255
[58] Field of Search ........................... 604/9, 30–34, 604/65, 67; 222/215, 255, 262, 263, 372

[56] References Cited

U.S. PATENT DOCUMENTS

| | | | |
|---|---|---|---|
| 4,207,871 | 6/1980 | Jenkins | 604/65 |
| 4,411,651 | 10/1983 | Schulman | 604/67 |
| 4,447,224 | 5/1984 | Decant et al. | 604/67 |
| 4,474,309 | 10/1984 | Solomon | 604/67 |
| 4,486,190 | 12/1984 | Reinicke | 604/67 |
| 4,673,391 | 6/1987 | Kondo et al. | 604/67 |
| 4,710,177 | 12/1987 | Smith et al. | 604/9 |

FOREIGN PATENT DOCUMENTS 0197705 10/1986 European Pat. Off. .............. 604/30

OTHER PUBLICATIONS

"An Electronically Controlled Piezoelectric Insulin Pump and Valves", Spencer et al., 1978 IEEE.

Primary Examiner—Max Hindenburg

[57] ABSTRACT

A silicon micropump which can be manufactured by established integrated circuit techniques, and which is provided with piezoelectric valves, is described. The micropump can be used to pump liquids or gases at a very low rate, which can be accurately prescribed. The body of the pump and the valves are made in silicon and glass, while the valves contain piezoelectric material, which allows opening and closing of the valves by electrical means.

10 Claims, 7 Drawing Sheets

PIEZOELECTRIC MICROPUMP WITH MICROVALVES

BACKGROUND OF THIS INVENTION

The present invention concerns a micropump with at least two valves and at least one pushing member, while said valves and said pushing members contain which is electrically controlled. A known micropump of the prior art is described in the article "An Electronically Controlled piezoelectric Insulin Pump and Valves." by W. J. Spencer, e.a., IEEE Transactions on Sonics and Ultrasonics, vol SU-25, No 3 May 1978, p153–156.

This known pump of which the stated purpose is the administering of insulin to diabetes patients, has some drawbacks. It is made on the basis of a well known principle, namely the use of an inlet valve and an outlet valve, while said inlet valve and said outlet valve can be opened and closed selectively. The valves and the pushing member are constructed as socalled bimorphs (two polarized piezoelectric elements joined together and mounted between electrodes in such a way, that when an electric voltage is applied, the constellation bends into a concave or convex shape, depending on the polarity of the electric voltage), or as single piezoelectric elements attached to e.g. a metal membrane. Said single piezoelectric elements attached to a metal membrane are called enakemesomorphs. Said enakemesomorphs also have the property that when an electric field is applied to them, while they are in a mechanically stable equilibrium position, e.g. a flat position, they assume a position, deflected from the original equilibrium position, which is either convex or concave, albeit that the deflection is less for a given electric voltage, than that of a bimorph of the same dimensions and containing identical piezoelectric material.

Said pump, hereafter referred to as the Spencer pump, has the disadvantage that special precautions have to be taken to ensure that the valves, which are surrounded by a liquid, are electrically isolated from the liquid to prevent hydrolysis. Further, this pump has been made using conventional assembly techniques, resulting in a pump which is rather large and heavy and unsuitable for implantation in a patient. Moreover, these assembly techniques are not very economical, leading to pumps which are rather expensive.

The present invention has the purpose of providing a means in which small amounts of a liquid or a gas can be pumped from a reservoir into a recipient medium. The liquid could be a medical drug, a coolant or a refrigerant, a fuel in a fuel consuming engine, or a liquid used in a chemical or biological process. Many other applications can be conceived.

The present invention has been stimulated by the need for an implantable insulin pump for diabetes patients, but it has a wider field of application. As the interior of the pump consist of silicon and glass, while the silicon is oxidized, we can state that the parts of the pump which are exposed to the medium which has to be pumped, are hardly or not at all susceptible to corrosion when acids, solvents, or aqueous solutions are present in its interior. Exceptions are some alkaline materials, and hydrogenfluoride, which will etch the silicondioxide and the glass.

SUMMARY OF THE INVENTION

Accordingly, the present invention provides a semiconductor micropump with microvalves and a process for the fabrication thereof, which overcomes many of the disadvantages of the previously mentioned Spencer pump.

An objective of the invention is to design a silicon micropump in such a manner that it can be fabricated by using techniques particularly oriented towards massproduction An other objective of the pump with its valves is to design it so that can be manufactured in a simple fashion, to achieve an economical product.

A third objective of the pump with valves is that it can be used as an accurate dosage unit.

A fourth objective of the invention is to create a pump which is very suitable to miniaturization. This is of special importance for medical purposes, when space and weight requirements are very tight.

A fifth objective of the invention is to provide a silicon pump, which can be totally integrated: as the mechanical parts of the pump are made of silicon, the electronic control system of the pump can also be made in the same silicon, by using the conventional integrated circuit techniques.

DESCRIPTION OF THE INVENTION

This invention provides a micropump, made in silicon, by etching a channel at the front or backside of a wafer, that terminates at the valves, or at the pushing member. A distinctive feature of the pump is that the valves and the pushing member are physically identical, they are arranged in series, while they are all individually controllable by the electronic control circuit.

A pump like this can be made in particular as existing mainly of a wafer with an etched first channel, that reaches the surface of the wafer at a valve/pushing member and terminates there. A second channel starts at said valve/pushing member, but is not an extension of said first channel The connection between said first channel and said second channel is made by means of the valve/pushing member, which can be open or closed by an electronic control voltage.

A preferred embodiment of the pump contains a silicon wafer, in which the channel has been etched at the backside. Said channel consists of an etched trough, which has been closed at its open side by the attachment to the silicon of a plate of a suitable type of glass. Said attachment in the preferred embodiment is obtained in the process which is known as anodic bonding or Mallory bonding.

This preferred embodiment allows the usage of several well established I.C. processing techniques. These are known techniques, which are generally applied in semiconductor manufacturing operations, which makes these techniques attractive, because their possibilities and limitations are extensively described in the technical literature.

An advantage of the preferred embodiment is that in the silicon of which the pump has been made, the entire control circuit or a part thereof can be integrated, because the same techniques are used for the fabrication of the mechanical parts as for the fabrication of the eletronic circuit.

In the preferred embodiment a valve is made mainly as a surface depression, which can be circular or rectangular, or have other shapes, the topview of the depression is not of great importance, while in said depression a silicon rim in the form of a closed loop has been erected or has not been depressed. This rim extends substantially to the same height as the original surface of the wafer.

Mainly concentric with said rim, although not necessarily so, a first hole has been etched all the way through the wafer, or at least in such a way that this hole reaches the first connecting channel.

A similar second hole has been etched in the area between the edge of the depression and the rim, said second hole etched in such a way that it connects to the second channel.

In the preferred embodiment the top of the pump is closed by a glass plate by the same process as used for closing the backside, namely anodic bonding.

Other methods of closing can also be used, e.g. a method in which the valves are individually treated as opposed to the integrated method of closing can be envisioned.

In the preferred embodiment in which the top side of the wafer is covered with glass, it has to be avoided that the glass cover will be bonded to the rim, because this will prohibit the operation of the pump.

To ascertain that the glass plate would not be bonded to the rim, the technique of selective bonding has been developed. In this technique, an area of which bonding to the glass plate is not desired, is left with a coating of SiO2. As the bonding effect is accomplished by the presence of a strong electric field in the gap between the glass and the silicon, a decrease of the electric field due to the presence of the SiO2 coating on the rim prevents the bonding of the rim to the glass.

When the glass is bonded to the wafer, the adjustment of the electric field has to be done carefully such that the bare silicon area does bond, while the coated area does not.

The displacement of the liquid or the gas can be accomplished by means of piezoelectric bimorphs, as described in the paper by Spencer. In that case the bimorphs are attached substantially at their edge or rim. Otherwise, displacement can also be reached by means of a so called enakemesomorph (from Greek ena ke meso=one a half). An enakemesomorph consist of a piezoelectric element attached to a non piezoelectric material. If the piezoelectric material expands due to an electric field, the non-piezoelectric material resists the expansion, and as a result a moment builds up, which bends the entire structure. An enakemesomorph can be used to advantage, in this case because its requires no additional shielding of the bottom electrode of the bending element, because the bottom element now can be chosen to be glass, the glass that is used to cover the top of the wafer.

When an enakemesomorph of which the top element is the piezoelectric element, must bend upward, it is sufficient to apply a positive voltage to said piezoelectric element. Under said positive voltage said element will expand, while its nonpiezoelectric counterpart resists the expansion, and the resulting moment will cause the bending. Associated with the bending there is an expansion of both elements, which is beneficial for the bending process if the element is clamped at its edges, because the bent shape requires the beam to be longer then the flat shape. In the case of an enakemesomorph in the form of a substantially circular or rectangular plate, clamped at its contour, the diameter should be longer in order to bend.

In the case that an enakemesomorph must bend downward, it is not sufficient to apply a negative voltage to the electrode of the piezoelectric top element, because that would cause said element to contract, and with it, it would require the bottom element to contract too, decreasing the total length of the enakemesomorph, which will resist the tendency of this combination to bend downward if the enakemesomorphh is clamped at its edges.

To avoid this problem we have invented two improvements of the enakemesamorph.

First the solid enakemesomorph with a separate inner and outer electrodes configuration. The inner and outer electrode are electrically in parallel when the enakemesomorph has to bend upward, but are given the opposite polarity when the enakemesomorph has to bend downward. As a result, the outer electrodes, in the downward bending mode, cause the enakemesomorph at its outer rim to expand, resulting in a convex area at the outer edge, while the inner electrodes cause the enakemesomorph to contract in the area between said inner electrodes, causing it to bend concave at the location of the inner electrodes.

The area of the enakemesomorph that is contracted is now reduced from the entire area to the area between the inner electrodes, which gives the enakemesomorph a greater length, which facilitates the bending and allows a greater deflection.

The second type, the doughnut type enakemesomorph, has an annular piezoelectric body, and has a hole in the middle. The electrodes are again separated in an outer set and an inner set.

In this configuration, the glass plate is essentially in a clamped-clamped position, and an expansion of the piezoelectric body will not straightforwardly result in bending in either direction, because of the ambiguity of bending up or down, it may "oilcan", in a direction which can not be predicted. This ambiguity can be removed, by exciting the inner and outer electrodes different. To bend it upward, the outer area is first electrically contracted, without any voltage to the inner set of electrodes. This results in a concave shape of the outer area, and a small upward deflection of the enakemesomorph. Next the inner area is expanded, which will cause a convex form of the inner area, and increase the deflection of the bender. Following this, the voltage on the outer area is reversed, which causes this area to expand too, thereby increasing the deflection.

To bend it downward, the outer area is first expanded, which will cause a small downward deflection of the bender, after which the inner area is expanded too, resulting in a larger downward deflection. The hole in the center of the piezoelectric disk reduces the bending resistance, resulting in an even larger deflection than without the hole.

It is useful to make the internal surfaces of the pump which are in contact with the medium which is pumped, as good as possible chemically inert. This extends the lifetime of the pump, and minimizes leakages due to reduced wear of critical surfaces, such as sealing rings. In addition, it reduces the possibility that the medium which is pumped is contaminated by the material of which the pump has been manufactured.

The invention will now be described in further detail by way of example only, and with reference to the accompanying drawings.

Figure 1:
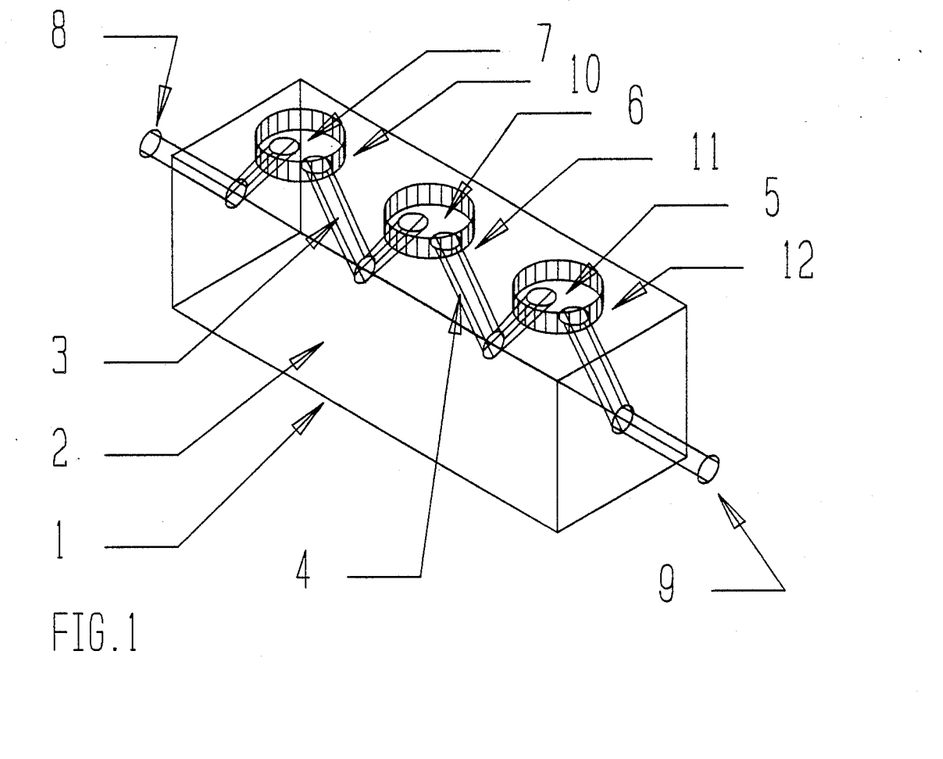
FIG. 1 shows an embodiment of an early prototype of the pump according to this invention, not in integrated form, partly in perspective, and partly in exposed view.

FIG. 1 shows a pump 1, which consists of a body 2, which contains a plurality of channels 3 which comes to the surface 4 at three locations, 5, 6 and 7. The channel 3 is connected to an inlet tube 8 and an outlet tube 9.

Hermetically connected to the surface 4, at 5, 6 and 7, piezoelectric bimorphs are located, which can be moved by electrical means, from the stable equilibrium position in which they are resting flat against surface 4, into a deflected position, in which said bimorphs have a convex shape.

The embodiment according to FIG. 1 operates in the following manner:

First the piezoelectric bimorph 10 is deflected electrically into a convex form, which sucks the medium which is to be pumped from the inlet tube 8 into the cavity formed under the convex shape of the bimorph. This cavity is now in an open connection with the channel 3 and the inlet tube 8.

Next the element 11 is deflected into a convex shape similar to element 10. This allows said medium to flow into the cavity formed under element 11.

Next element 10 is closed by shorting the voltage of this element to zero or by giving this element a negative voltage. An amount of said medium is now stored under element 11.

Then element 12 is deflected, which brings channel 3 in open connection with the outlet tube 9. The voltage of element 11 is removed, and element 11 will move downward, pushing said amount of said medium into channel 3, from which it is free to flow past the opened element 12 into the outlet tube 9. Finally, element 12 is put into its rest position, by removing the voltage required to maintain it deflected. The three elements are now closed again, and one complete cycle of the pump has been finished. A new pumping cycle can start from this point.

This very short explanation may suffice to indicate the principle of operation of the piezoelectric micropump according to the present invention.

Figure 2:
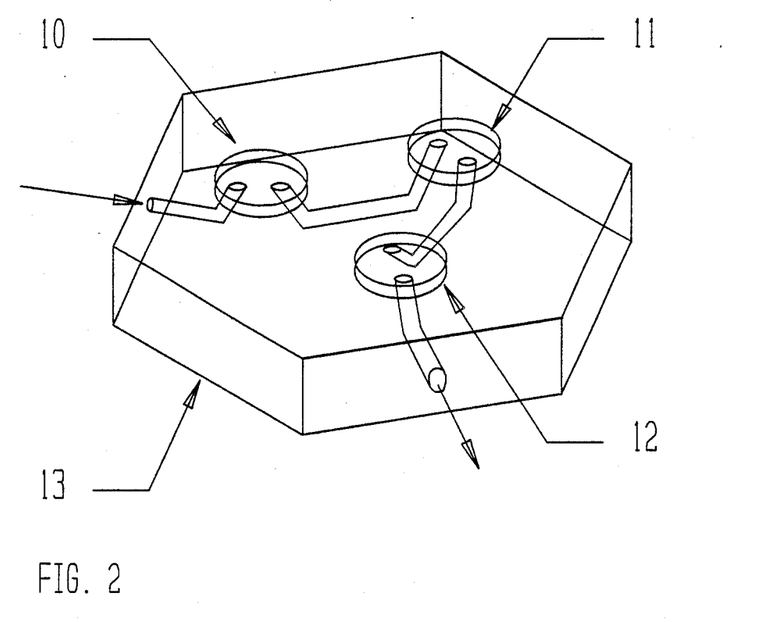
FIG. 2 shows a perspective view of a variation of the early prototype of the pump.

FIG. 2 shows a pump 13 of the same type as 1 according to FIG. 1. Pump 13 is different from pump 1 in that it is not rectangular in shape, but substantially triangular, which will make it easier to fit the pump into a circular package with essentially a low unused volume in the package.

Figure 3:
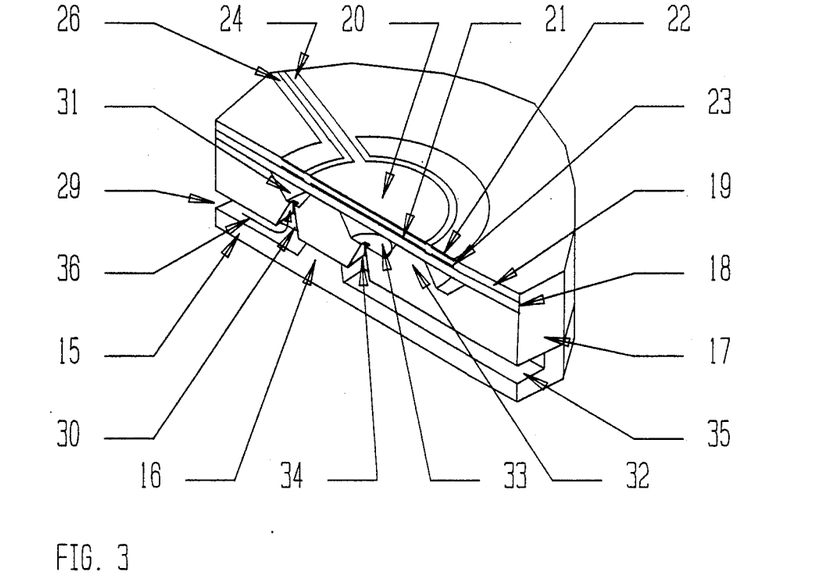
FIG. 3 shows partially a cross section and partially a perspective view of a part containing a valve of the pump according to a preferred embodiment of the present invention.

FIG. 3 shows a construction of a part of the pump, consisting of a glass bottom carrier 15, with local elevations 16, which support a silicon wafer 17, which carries a glass membrane 18 on which a piezoelectric disk 19 has been attached. Said piezoelectric disk 19 has a set of inner top and bottom electrodes 20 and 21, and a set of outer top and bottom electrodes 22 and 23. The inner electrodes 20 and 21 are connected to the electrical control circuit by means of two connections, of which only the top one 24 is shown. The outer electrodes are connected to the control circuit by two connections of which also only the top connection 26 is shown.

The glass membrane 18 has been attached to the top surface 28 of the silicon wafer 17 by anodic bonding. An inlet channel 29 is located between the glass carrier 15 and silicon wafer 17. This channel can be made by etching it either in the wafer 17 or in the glass plate 15 or both. The inlet channel 29 connects to an orifice 30 which has been etched all the way through the wafer 17, said orifice 30 is again connected to a depression 31 in the surface 28 of the wafer. Said depression 31 contains in its center a ring shaped elevation 32, which separates depression 31 from a substantially concentric depression 33, which is connected with an orifice 34, which has been etched, like orifice 30, through the entire thickness of the wafer. Orifice 34 is now connected to an outlet channel 35.

It will be clear, after the explanation that accompanied FIG. 1, that the inlet channel 29 can be connected to the outlet channel of a previous pumping element, or to an inlet connection which is connected to a reservoir which contains the medium which has to be pumped. Similarly, an outlet channel 35 can be connected to the inlet channel of a following pumping element, or to an outlet tube, which conducts the medium into the recipient of the pump.

Figure 4:
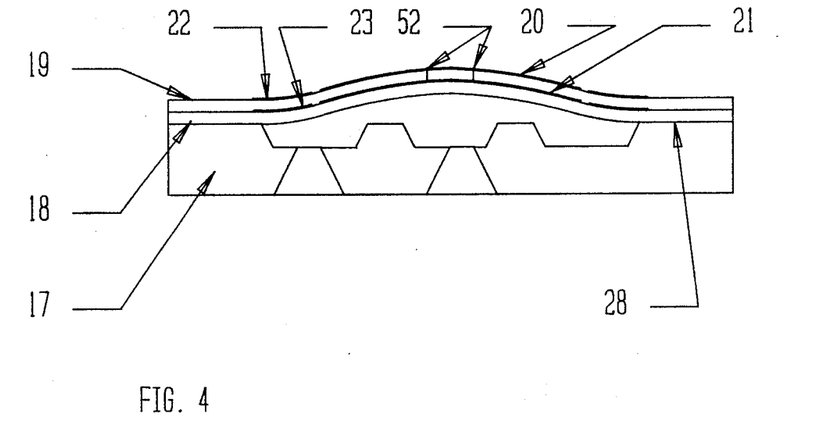
FIG. 4 is a cross section of an enakemesomorph, presented here to facilitate an explanation of its operation

FIG. 4 shows a cross section of the glass membrane 18, which is anodically bonded to the surface 28 of the silicon wafer 17, with the piezoelectric disk 19, substantially concentric with the substantially circular contour, which defines the non-bonded area of the glass membrane.

As is shown in FIG. 4, we can obtain a convex shape of the combination of the glass membrane 18 and the piezoelectric disk 19, by applying for example, given an appropriate polarization direction of the piezoelectric material, a positive voltage between the electrodes 20 and 21 as well as between 22 and 23 (electrode 20 and 22 more positive than 21 and 23). If we neglect the width of the spacing between the inner an outer set, the result of the application of the voltage will be as if said spacing did not exist, and electrodes 20 and 22 were connected in parallel with 21 and 23, covering the entire electroded disk.

As a result of said positive voltage on electrodes 20 and 22 with respect to electrodes 21 and 23, the piezoelectric material between these four electrodes tends to expand sideways, while at the same time the thickness of said piezoelectric material will decrease. Said sideways expansion is hindered by the glass membrane 18, which resists said sideways expansion, but can only build up sufficient resistance to the stress of the piezoelectric disk 19 by deforming elastically. If the piezoelectric disk is not allowed to expand to the contour it would obtain if it were totally free, it will remain under compressive strain.

In the process of elastic deformation of the glass membrane, a tensile force builds up in the glass with such a magnitude that an equilibrium is formed by the compressive forces in the piezoelectric disk and the tensile forces in the glass membrane. As these forces are not in the same plane, but at a distance from each other, a moment is created by these forces and the distance between their points of action.

The resulting moment in the combination of membrane 18 and piezoelectric material 19 causes that said combination assumes a convex form. The formation of said convex form is facilitated by the excess length which the combination of the glass membrane 18 and the piezoelectric disk 19 have obtained, due to the sideways elongation of both of these elements.

On the other hand, if a concave shape of the combination is desired, a negative voltage to the electrodes may be applied, in an analogous fashion to when the positive voltage was applied when a convex shape was the goal. The piezoelectric disk will contract sideways, and increase its thickness, and again it will force the underlying glass membrane 18 to yield elastically, and thus build up a moment, which causes it to assume a concave shape. However, as the sides of the glass membrane 18 are anodically bonded to the the surface 28 of the silicon wafer 17, a sideways contraction of the glass will increase the tensile stress in the glass membrane in the area between the rim of the piezoelectric disk, and the edge of the area where the glass membrane had been anodically bonded, and as a result the bending due to the moment will be counteracted by this tensile stress in forming the concave shape, rather then facilitated as was the case with the positive voltage when a convex shape was our goal.

To alleviate this counteraction of the tensile stress, the separation of the inner and outer set of electrodes has been devised. If a concave shape is required from the combination, a positive voltage is applied to the outer electrode set 22 and 23, causing the material between these electrodes to expand, and to bend convex the area of the outer set. In addition a negative voltage is applied to the set 20 and 21, which causes the area between the inner set of electrodes to contract, and to bend said area concave.

The sideways expansion of the area between the outer set of electrodes can be offset by the sideways contraction of the area between the inner set of electrodes, leaving the total length substantially unchanged.

A positive voltage on the outer set that is considerably larger in magnitude than the negative voltage of the inner set may even increase the total length and thus facilitate the formation of the concave form.

When the piezoelectric disk has been made in the doughnut shape, as indicated by the contours of the hole in the doughnut 52, the resistance to bending in the center of the valve has been decreased, which further facilitates the downward bending of the glass plate.

After this explanation it will be clear that a configuration with at least three of these elements according to FIG. 3, a pumping action can be obtained, which is indicated with arrows 36. Application of the required voltages in the proper order can result in a pumping action as shown with arrows 36, but it will be clear that the pumping action can be reversed, by reversing the sequence of the voltages on the pumping elements.

Figure 5:
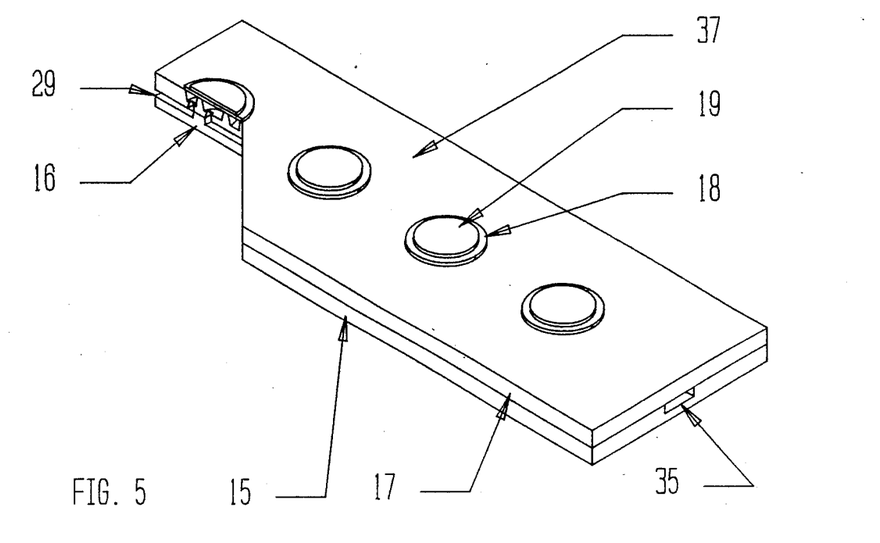
FIG. 5 is a drawing of a partially exposed perspective view of an other embodiment.

FIG. 5 shows shows a pump 37 which consists of a series connection of pumping elements according to FIG. 3.

Figure 6:
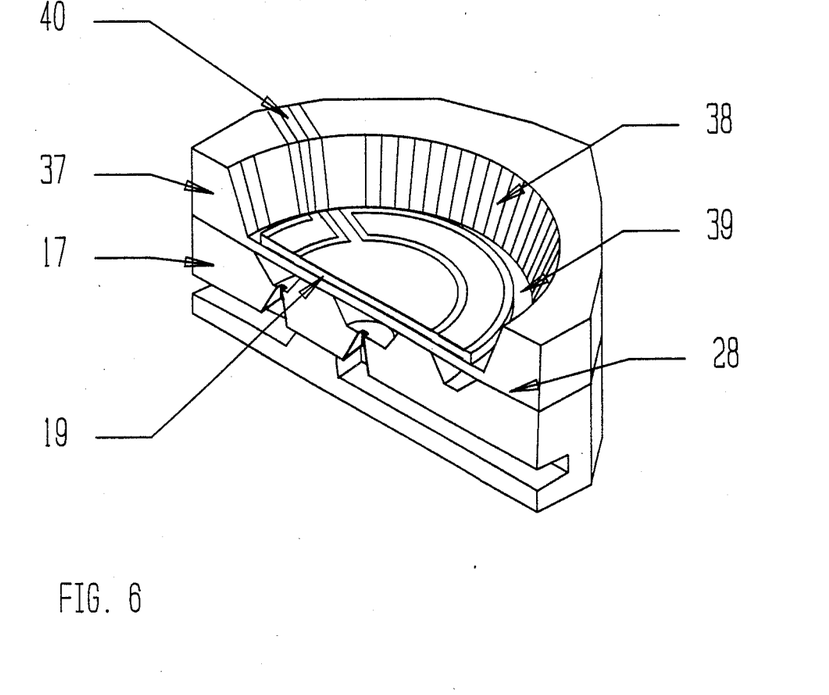
FIG. 6 shows partially a cross section and partially a perspective view of a further embodiment.

FIG. 6 displays an integrated variation of the pumping element according to FIG. 3. Corresponding elements of the pumping membrane are therefore indicated with corresponding numbers.

The silicon wafer 17 carries at its upper surface 28 a wafer 37 of silicon. This wafer contains depression 38 such that the bottom 39 of this depression forms a membrane similar to the glass membrane 18 of FIG. 4. The piezoelectric disk 19 consists of sputtered, or otherwise deposited material, like zincoxide, and has again electrodes 20, 21, 22 and 23. The bottom electrodes 21 and 23 and their connections 40 to the control circuit 43 are deposited to the topsurface of the membrane 39. The control circuit may consist of an integrated circuit which has been manufactured in the same wafer 37 as the membrane, or in wafer 17 which contains the pumpchambers.

Figure 7:
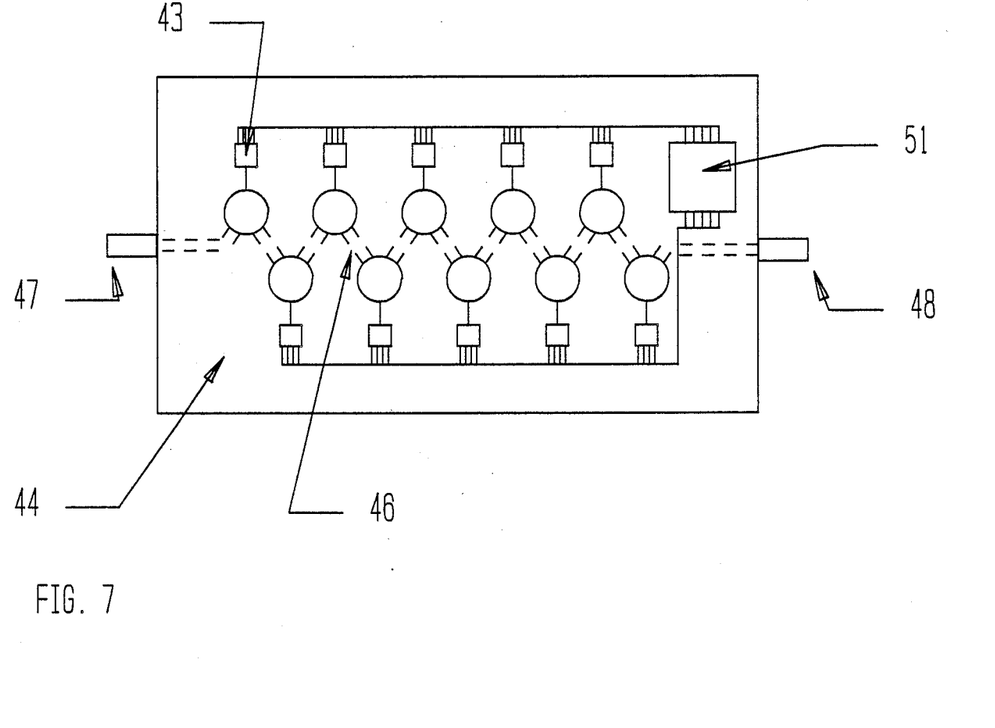
FIG. 7 is schematic drawing showing a completely integrated pump according to this invention.

FIG. 7 shows a top view of a fully integrated pump 44 in the form of a layered disk similar to FIG. 6 in which a channel 46 and an inlet connection 47 have been made as well as an outlet connection 48. Pump 44 has been provided with ten pumping elements of the type shown in FIG. 6. The integrated circuits 43 are connected by means of conducting leads to a central control circuit 51.

It should be noted that all material parts in contact with the liquid which is to be pumped are chemically relatively stable, and electrically insulated. With reference to FIG. 5, these are particularly the walls of the inlet channel 29 and outlet channel 35; referring to FIG. 3 said surfaces are bordering the orifices 30 and 34, the depression in the surface 31 and 33, the elevation ring 32; further referring to FIG. 6, it is and the lower surface of diaphragm 39. Insofar as the surfaces are of glass they are already relatively chemically inert, except for such acids as hydrofluoride, while the surfaces of the silicon are oxidized to SiO2 which has similar chemical properties as glass.

A special control circuit can operate the pumping elements in such a manner that a "string of beads" of fluid are pumped, e.g. in a pump with ten members the first five members may be consecutively opened to suck in the fluid and store it under the first five open valves. Then the sixth member could open, while the first member closes, which would push the liquid under members two through six. This way the string could be passed on through the pump. In the event that one valve would be slightly leaking, this would have little effect on the overall performance of the pump, because there are always be more than one members closed (in this example five).

A configuration of two or more pumps, connected in parallel, pumping from different sources, but into one outlet channel, can achieve mixing of the two or more fluids pumped by said combination of the two or more pumps. Said combination may reside physically on one and the same wafer. The mixing ratio can be prescribed by the pumping rates of the individual pumps of said combination of pumps.

The pumping rate can be chosen by suitable manipulation of the following parameters:

1. the controlling voltages on the displacing members/valves,
2. the cycle frequency of the pump
3. the phase relation of the voltages controlling the pumpelements
4. the number of elements under which the fluid is stored Failsafe characteristics of the pump can be obtained by buiding into the valves/displacing members a static tensile or compressive stress. In the case of the pump according to FIG. 6 the bottom of membrane 39 can be oxidized to SiO2. This causes a compressive stress in the SiO2 film which will cause the membrane to bend down, even without any voltage applied. Alternatively, the inner sealing ring 32 can be made a little higher to ensure that the the membrane in its rest position is pressed firmly against the sealing ring.

What is claimed is:

1. A pump for the displacement of a liquid, comprising:
    a body of a silicon wafer, said wafer having a front side and a back side, said front side having an original front surface plane and said back side having an original back surface plane, while in said front side are shaped by a first means for removing from said front side a multiplicity of surface depressions in each of which at lest one rim of substantially circular shape extends from the bottom of said surface depression to said original front surface plane,
    and in which are shaped by a second means for removing from said backside:
        a multiplicity of troughs,
    and in which are shaped by a third means for removing from said backside:
        a pair of passage holes which extend from two of said troughs to said original front surface plane,
        a multiplicity of passage holes which extend from said troughs to said surface depressions;
    a front side glass plate with an upper and a lower surface in which a first hole for the admission of said liquid into the pump and a second hole for the removal of said liquid are made, said front side glass plate being hermetically connected with said lower surface by a joining means to said original front surface of said silicon wafer over the entire area of said original front surface, using an exclusion means to exclude said rim from being joined to said lower surface;
    a backside plate which is hermetically connected to said original backside of said silicon wafer by said joining means, with the exclusion of said troughs and said passage holes;
    a multiplicity of piezoelectric disks having a free surface and a joined surface, said joined surface being joined to said upper side of said front side glass plate, substantially such that said piezoelectric disks oppose said surface depressions;
    a multiplicity of electrodes consisting of a first set located on said free surface of said piezoelectric disks, and a second set located on said joined surface;
    a multiplicity of electric conductor connections to said sets of electrodes.

2. A pump as claimed in claim 1, in which said joining means for joining said lower surface of said front side glass plate to said original front surface of said silicon wafer is the anodic bonding method.

3. A pump as claimed in claim 1, in which said joining means for joining said back side glass plate to said original back side surface of said silicon wafer is the anodic bonding method.

4. A pump as claimed in claim 1 in which said exclusion means for the prevention of joining said rim to said lower surface of said front side glass plate consists of providing a film of Silicondioxide on the upper surface of said rim.

5. A pump as claimed in claim 1, in which said first means for removing used to shape said surface depressions in said front side of said wafer consists of one of the following methods:
    isotropic etching,
    anisotropic etching.

6. A pump as claimed in claim 1, in which said second means for removing said troughs consists of one of the following methods:
    isotropic etching,
    anisotropic etching,
    while said third means for removing used to shape said passage holes is the anisotropic etching method.

7. A pump as claimed in claim 1, in which said multiplicity of electrodes consists of a first and a second pair of electrodes, said first pair being arranged in the form of two opposing disks and said second pair arranged in the form of two rings which are substantially concentric with said opposing disks, which allows the annular area of said piezoelectric disk located between said second pair of electrodes, to expand, while the area of said piezoelectric disk between said first pair of electrodes contracts.

8. A pump as claimed in claim 1, in which said surface depressions are shaped after the entire front surface of said wafer with the exclusion of said rim, has been removed to a depth of 3–5 micrometers, resulting in said rim having a height above said bottom of said surface depressions that is larger than the height of the front surface surrounding said surface depressions, which causes said front side glass plate to be permanently bent over said rim, after said front side glass plate has been joined to said front surface.

9. A pump as claimed in claim 1, in which said piezoelectric disks have a hole in their center, which reduces their bending stiffness.

10. A pump as claimed in claim 1, in which the surfaces of the pump contacting said pumped liquid, consist of Silicondioxide which has the property of being chemically inert.

* * * * *